United States Patent
Ohnemus et al.

(10) Patent No.: US 11,158,407 B2
(45) Date of Patent: *Oct. 26, 2021

(54) AUTOMATED HEALTH DATA ACQUISITION, PROCESSING AND COMMUNICATION SYSTEM AND METHOD

(71) Applicant: dacadoo ag, Zurich (CH)

(72) Inventors: Peter Ohnemus, Herrliberg (CH); Andre Naef, Zurich (CH); Laurence Jacobs, Thalwil (CH); David Leason, Chappaqua, NY (US)

(73) Assignee: DACADOO AG, Zurich (CH)

( * ) Notice: Subject to any disclaimer, the term of this patent is extended or adjusted under 35 U.S.C. 154(b) by 40 days.

This patent is subject to a terminal disclaimer.

(21) Appl. No.: 16/579,285

(22) Filed: Sep. 23, 2019

(65) Prior Publication Data

US 2020/0020429 A1    Jan. 16, 2020

Related U.S. Application Data

(63) Continuation of application No. 15/360,807, filed on Nov. 23, 2016, now Pat. No. 10,424,404.
(Continued)

(51) Int. Cl.
*G16H 10/60* (2018.01)
*H04L 29/08* (2006.01)
(Continued)

(52) U.S. Cl.
CPC ......... *G16H 10/60* (2018.01); *G06Q 30/0236* (2013.01); *G16H 20/30* (2018.01);
(Continued)

(58) Field of Classification Search
CPC . A61B 5/7264; A61B 5/0022; A61B 5/02438; A61B 5/0024; G06F 19/345;
(Continued)

(56) References Cited

U.S. PATENT DOCUMENTS

| 6,110,109 A | 8/2000 | Hu et al. |
| 6,454,705 B1 | 9/2002 | Cosentino et al. |

(Continued)

FOREIGN PATENT DOCUMENTS

| CN | 101075274 | 11/2007 |
| EP | 0709058 | 5/1996 |

(Continued)

OTHER PUBLICATIONS

Matsubara, Atsushi, "12 Months of Macintosh—Broaden Your Lifestyle with Mac—Jun. 6, "Fitness with Mac&iPod"", Mac Fan, Japan, Mainichi Communications Inc., Jul. 1, 2008, vol. 16, No. 7, pp. 146-151.

(Continued)

*Primary Examiner* — Reginald R Reyes
(74) *Attorney, Agent, or Firm* — Leason Ellis LLP

(57) ABSTRACT

A passive tracking device, a processor configured to receive information from the tracking device, and a database accessible by the processor, among other elements, are disclosed. A first activity unit having a first start time corresponding to detection of engagement is monitored. The processor is further configured to establish a first end time of the first activity unit using the monitored information, and automatically ascribe a classification of the first activity unit. The classification of the first activity unit is output to a display of a computing device, and the classification of the first activity unit is stored in the database. A revised classification is output to a display of a computing device, the revised classification is stored in the database.

18 Claims, 14 Drawing Sheets

Related U.S. Application Data

(60) Provisional application No. 62/259,593, filed on Nov. 24, 2015, provisional application No. 62/269,808, filed on Dec. 18, 2015, provisional application No. 62/341,421, filed on May 25, 2016, provisional application No. 62/383,027, filed on Sep. 2, 2016, provisional application No. 62/409,329, filed on Oct. 17, 2016.

(51) Int. Cl.
*G16H 20/30* (2018.01)
*G16H 40/67* (2018.01)
*H04W 4/21* (2018.01)
*G06Q 30/02* (2012.01)
*G06Q 50/00* (2012.01)
*G16H 50/30* (2018.01)
*G16H 50/70* (2018.01)

(52) U.S. Cl.
CPC ............ *G16H 40/67* (2018.01); *H04L 67/22* (2013.01); *H04L 67/306* (2013.01); *H04W 4/21* (2018.02); *G06Q 50/01* (2013.01); *G16H 50/30* (2018.01); *G16H 50/70* (2018.01)

(58) Field of Classification Search
CPC ............ G06F 19/3418; G06F 19/3481; G06F 19/3431; G06F 19/3443
See application file for complete search history.

(56) References Cited

U.S. PATENT DOCUMENTS

| | | | |
|---|---|---|---|
| 6,514,199 B1 | 2/2003 | Alessandri | |
| 6,616,578 B2 | 9/2003 | Alessandri | |
| 6,643,531 B1 | 11/2003 | Katarow | |
| 6,702,719 B1 | 3/2004 | Brown et al. | |
| 6,751,657 B1 | 6/2004 | Zothner | |
| 7,024,370 B2 | 4/2006 | Epler et al. | |
| 7,034,691 B1 | 4/2006 | Rapaport | |
| 7,261,690 B2 | 8/2007 | Teller et al. | |
| 7,426,492 B1 | 9/2008 | Bishop | |
| 7,617,128 B2 | 11/2009 | Greak | |
| 7,628,730 B1 | 12/2009 | Watterson et al. | |
| 7,904,310 B2 | 3/2011 | Brown | |
| 8,073,708 B1 | 12/2011 | Igoe | |
| 8,075,450 B2 | 12/2011 | Fabbri et al. | |
| 8,135,863 B2 | 3/2012 | Nekovee | |
| 8,157,731 B2 | 4/2012 | Teller et al. | |
| 8,419,650 B2 | 4/2013 | Cosentino | |
| 8,706,530 B2 | 4/2014 | Ohnemus et al. | |
| 8,712,510 B2 | 4/2014 | Quy | |
| 9,052,798 B1 | 6/2015 | Klassen | |
| 9,533,228 B2 | 1/2017 | Dugan | |
| 9,744,441 B2 | 8/2017 | Klassen | |
| 9,801,553 B2 * | 10/2017 | Chadderdon, III | A61B 5/7264 |
| 10,402,792 B2 | 9/2019 | Lin et al. | |
| 10,424,404 B2 | 9/2019 | Ohnemus et al. | |
| 2001/0049470 A1 | 12/2001 | Mault et al. | |
| 2002/0047867 A1 | 4/2002 | Mault et al. | |
| 2002/0055418 A1 | 5/2002 | Pyles et al. | |
| 2003/0154171 A1 | 8/2003 | Karp et al. | |
| 2004/0133081 A1 | 7/2004 | Teller et al. | |
| 2004/0139208 A1 | 7/2004 | Tuli | |
| 2004/0172290 A1 | 9/2004 | Leven | |
| 2004/0180708 A1 | 9/2004 | Southard | |
| 2005/0060194 A1 | 3/2005 | Brown | |
| 2005/0076301 A1 | 4/2005 | Weinthal | |
| 2005/0165618 A1 | 7/2005 | Nerenberg | |
| 2005/0203773 A1 | 9/2005 | Soto et al. | |
| 2005/0228692 A1 | 10/2005 | Hodgdon | |
| 2005/0289590 A1 | 12/2005 | Cheok et al. | |
| 2006/0080149 A1 | 4/2006 | Takada et al. | |
| 2006/0206013 A1 | 9/2006 | Rothman et al. | |
| 2006/0282021 A1 * | 12/2006 | DeVaul | A61B 5/1117 600/595 |
| 2006/0293573 A1 | 12/2006 | Bardy | |
| 2007/0016449 A1 | 1/2007 | Cohen et al. | |
| 2007/0027367 A1 | 2/2007 | Oliver et al. | |
| 2007/0063850 A1 * | 3/2007 | Devaul | A61B 5/0205 340/573.1 |
| 2007/0161868 A1 | 7/2007 | Root | |
| 2007/0168230 A1 | 7/2007 | Roman | |
| 2007/0276203 A1 | 11/2007 | Day | |
| 2008/0089666 A1 | 4/2008 | Aman | |
| 2008/0146892 A1 | 6/2008 | Leboeuf et al. | |
| 2008/0162088 A1 * | 7/2008 | DeVaul | A61B 5/0024 702/190 |
| 2008/0183595 A1 | 7/2008 | Sakamoto | |
| 2009/0105047 A1 | 4/2009 | Guidi et al. | |
| 2009/0105550 A1 | 4/2009 | Rothman | |
| 2009/0113016 A1 | 4/2009 | Sen et al. | |
| 2009/0149717 A1 | 6/2009 | Brauer et al. | |
| 2009/0156363 A1 | 6/2009 | Guidi et al. | |
| 2009/0163774 A1 | 6/2009 | Sudeesh et al. | |
| 2009/0209393 A1 | 8/2009 | Crater et al. | |
| 2009/0300171 A1 | 12/2009 | Bhame et al. | |
| 2010/0004945 A1 | 1/2010 | Petratos et al. | |
| 2010/0004947 A1 | 1/2010 | Nadeau et al. | |
| 2010/0082362 A1 | 4/2010 | Salsbury et al. | |
| 2010/0160743 A1 | 6/2010 | Jeong et al. | |
| 2010/0220914 A1 | 9/2010 | Iwase et al. | |
| 2010/0285821 A1 | 11/2010 | Smeeding | |
| 2010/0287011 A1 | 11/2010 | Muchkaev | |
| 2010/0324427 A1 | 12/2010 | Devot et al. | |
| 2011/0021936 A1 | 1/2011 | Luo | |
| 2011/0060576 A1 | 3/2011 | Sharma et al. | |
| 2011/0069615 A1 | 3/2011 | Zhang et al. | |
| 2011/0201902 A1 | 8/2011 | Shiga et al. | |
| 2011/0213664 A1 | 9/2011 | Osterhout et al. | |
| 2011/0288379 A1 | 11/2011 | Wu | |
| 2012/0042004 A1 | 2/2012 | Shenfield | |
| 2012/0094649 A1 | 4/2012 | Porrati | |
| 2012/0117018 A1 | 5/2012 | Miller | |
| 2012/0171649 A1 | 7/2012 | Wander et al. | |
| 2012/0179665 A1 | 7/2012 | Baarman et al. | |
| 2012/0191469 A1 | 7/2012 | Akradi | |
| 2012/0253489 A1 | 10/2012 | Dugan | |
| 2012/0296455 A1 | 11/2012 | Ohnemus et al. | |
| 2012/0313776 A1 | 12/2012 | Utter, II | |
| 2013/0031189 A1 | 1/2013 | Lam | |
| 2013/0080181 A1 | 3/2013 | DePetro | |
| 2013/0095459 A1 | 4/2013 | Tan | |
| 2013/0158367 A1 | 6/2013 | Pacione et al. | |
| 2013/0158368 A1 | 6/2013 | Pacione et al. | |
| 2013/0211858 A1 | 8/2013 | Ohnemus et al. | |
| 2013/0217979 A1 | 8/2013 | Blackadar et al. | |
| 2013/0252731 A1 | 9/2013 | Dugan | |
| 2013/0262357 A1 | 10/2013 | Amarasingham et al. | |
| 2013/0311197 A1 | 11/2013 | Hummer | |
| 2014/0088995 A1 | 3/2014 | Damani | |
| 2014/0099614 A1 | 4/2014 | Hu | |
| 2014/0110273 A1 | 4/2014 | Bar-Or et al. | |
| 2014/0114680 A1 | 4/2014 | Mills et al. | |
| 2014/0135592 A1 | 5/2014 | Ohnemus | |
| 2014/0156308 A1 | 6/2014 | Ohnemus et al. | |
| 2014/0180583 A1 | 6/2014 | Doherty et al. | |
| 2014/0180598 A1 | 6/2014 | Stivoric | |
| 2014/0188886 A1 | 7/2014 | Mahaffey et al. | |
| 2014/0214441 A1 | 7/2014 | Young et al. | |
| 2014/0221791 A1 | 8/2014 | Pacione | |
| 2014/0247135 A1 | 9/2014 | Proud | |
| 2014/0257047 A1 | 9/2014 | Sillay et al. | |
| 2014/0316801 A1 | 10/2014 | Oswald et al. | |
| 2014/0316811 A1 | 10/2014 | Ohnemus | |
| 2014/0324443 A1 | 10/2014 | Ricks et al. | |
| 2015/0095046 A1 | 4/2015 | Pironti et al. | |
| 2015/0169659 A1 | 6/2015 | Lee et al. | |
| 2015/0251074 A1 | 9/2015 | Ahmed | |
| 2015/0302439 A1 | 10/2015 | Morton et al. | |
| 2015/0312243 A1 | 10/2015 | Ponsford | |
| 2015/0332283 A1 | 11/2015 | Witchey | |
| 2016/0055236 A1 | 2/2016 | Frank | |

(56) References Cited

U.S. PATENT DOCUMENTS

| | | | |
|---|---|---|---|
| 2016/0089038 A1* | 3/2016 | Chadderdon, III | ............... A61B 5/02055 600/301 |
| 2016/0110813 A1 | 4/2016 | Hayden | |
| 2016/0293033 A1 | 10/2016 | Anderson-Hanley | |
| 2016/0354683 A1 | 12/2016 | Palmisano | |
| 2017/0039330 A1 | 2/2017 | Tanner, Jr. | |
| 2017/0091865 A1 | 3/2017 | Hayden | |
| 2017/0132626 A1 | 5/2017 | Kennedy | |
| 2017/0147775 A1 | 5/2017 | Ohnemus et al. | |
| 2017/0161439 A1 | 6/2017 | Raduchel | |
| 2017/0214675 A1 | 7/2017 | Johnsrud | |
| 2017/0266502 A1 | 9/2017 | Aragones | |
| 2017/0323392 A1 | 11/2017 | Kasper | |
| 2018/0028920 A1 | 2/2018 | Judkins | |
| 2018/0060496 A1 | 3/2018 | Bulleit | |
| 2018/0068083 A1 | 3/2018 | Cohen et al. | |
| 2018/0234496 A1 | 8/2018 | Ratias | |
| 2018/0311572 A1 | 11/2018 | Pickover | |
| 2018/0344215 A1 | 12/2018 | Ohnemus et al. | |
| 2018/0350451 A1 | 12/2018 | Ohnemus et al. | |
| 2019/0028264 A1 | 1/2019 | Bisti | |
| 2019/0164227 A1 | 5/2019 | Nicholson et al. | |
| 2020/0104935 A1 | 4/2020 | Schmitt et al. | |

FOREIGN PATENT DOCUMENTS

| | | |
|---|---|---|
| EP | 1087824 | 4/2001 |
| EP | 1259153 | 11/2002 |
| EP | 1400264 | 3/2004 |
| EP | 2025368 | 2/2009 |
| JP | 2007-122182 | 5/2007 |
| JP | 2010-113668 | 5/2010 |
| JP | 2010-157079 | 7/2010 |
| JP | 2012-063910 | 3/2012 |
| WO | WO 2004/032715 | 4/2004 |
| WO | WO 2004/095195 | 11/2004 |
| WO | WO 2007/112034 | 10/2007 |
| WO | WO 2009/026156 | 2/2009 |
| WO | WO 2012/050969 | 4/2012 |
| WO | WO 2011070831 | 4/2013 |

OTHER PUBLICATIONS

"Wii Fit", Famitsu DS Plus Wii, Japan, Enterbrain, Inc., Feb. 1, 2008, vol. 10, No. 2, pp. 18-19.

Ling Bao et al: "Activity Recognition from User-Annotated Acceleration Data". Mar. 23, 2004 (Mar. 23, 2004). Pervasive Computing; [Lecture Notes in Computer Science;;LNCS]. Springer-Verlag. Berlin/Heidelberg. pp. 1-17. XP019004314. ISBN: 978-3-540-21835-7 * the whole document * * in particular section 2 *.

Gyllensten I C et al: "Identifying Types of Physical Activity With a Single Accelerometer: Evaluating Laboratory-trained Algorithms in Daily Life" IEEE Transactions on Biomedical Engineering. IEEE Service Center. Piscataway. NJ. USA. vol. 1 • 58. No. 9. Sep. 1, 2011 (Sep. 1, 2011). pp. 2656-2663. XP011408471. ISSN: 0018-9294. DOI: 10.1109/TBME.2011.2160723 * the whole document * * in particular section II *.

Katherine Ellis et al: "Physical activity recognition in free-living from body-worn sensors". Proceedings of the 4th International Sensecam & Pervasive Imaging Conference on Sensecam '13. Nov. 18, 2013 (Nov. 18, 2013). pp. 88-89. XP055598839. New York. New York. USA DOI: 10.1145/2526667.2526685 ISBN: 978-1-4503-2247-8 * the whole document *.

Muthukumar Kumar: "Google's Activity Recognition API is awesome but where are the apps? —Geoawesomeness" Nov. 10, 2015 (Nov. 10, 2015). XP055599007. Retrieved from the Internet: URL:https:jjgeoawesomeness.comjgoogles-activity-recognition-api-is-awesome-but-where-are-the-apps/ [retrieved on Jun. 24, 2019] * the whole document *.

Anonymous: "CMMotionActivity—Core Motion : Apple Developer Documentation" Dec. 31, 2013 (Dec. 31, 2013). XP055599008. Retrieved from the Internet: URL:https://developer.apple.com/documentation/coremotion/cmmotionactivity [retrieved on Jun. 24, 2019] * the whole document *.

Bodhi Priyantha et al: "EERS: Energy Efficient Responsive Sleeping on Mobile Phones", International Workshop on Sensing for App Phones (PhoneSense), Nov. 2, 2010 (Nov. 2, 2010), XP055192517, Zurich, Switzerland Retrieved from the Internet: URL:http://sensorlab.cs.dartmouth.edu/phonesense/papers/PriyanthaEERS.pdf.

Brodersen et al., "Blockchain: Securing a New Health Interoperability Experience", Aug. 8, 2016; http://blocktonite.com/wp-content/uploads/2017/04/15-Winning-HHS-Papers-on-Blockchain-09.2016.pdf (Year: Aug. 2016).

* cited by examiner

AUTOMATED HEALTH DATA ACQUISITION, PROCESSING AND COMMUNICATION SYSTEM AND METHOD

CROSS-REFERENCE TO RELATED APPLICATIONS

The present application is a continuation of U.S. Non-Provisional patent application Ser. No. 15/360,807, filed Nov. 23, 2016, which is based on and claims priority to: U.S. Provisional Patent Application 62/259,593, filed Nov. 24, 2015, entitled AUTOMATED HEALTH DATA ACQUISITION, PROCESSING AND COMMUNICATION SYSTEM AND METHOD; U.S. Provisional Patent Application No. 62/269,808, filed Dec. 18, 2015, entitled AUTOMATED HEALTH DATA ACQUISITION, PROCESSING AND COMMUNICATION SYSTEM AND METHOD; U.S. Provisional Patent Application No. 62/341,421, filed on May 25, 2016, entitled AUTOMATED HEALTH DATA ACQUISITION, PROCESSING AND COMMUNICATION SYSTEM AND METHOD; U.S. Provisional Patent Application No. 62/383,027, filed on Sep. 2, 2016, entitled SYSTEM AND METHOD FOR ENCRYPTED HEALTH INFORMATION EXCHANGE; and finally U.S. Provisional Patent Application No. 62/409,329, filed on Oct. 17, 2016, entitled USER ACTIVITY TRACKING VIA INTEGRATION OF MOBILE COMPUTING DATA, each of which is incorporated by reference as if said forth in its respective entirety herein.

The present application further incorporates by reference U.S. patent application Ser. No. 14/257,855, filed Apr. 21, 2014 and entitled Automated Health Data Acquisition, Processing and Communication System, and U.S. patent application Ser. No. 14/094,616, filed Dec. 2, 2013 and entitled AUTOMATED HEALTH DATA ACQUISITION, PROCESSING AND COMMUNICATION SYSTEM, and further to U.S. patent application Ser. No. 14/079,495, filed Nov. 13, 2013 and entitled Health Band, the entire contents of each of which is respectively incorporated by reference as if expressly set forth in its entirety herein.

FIELD

The present application relates, generally, to automated health data acquisition and, more particularly, to automatically classifying health-related activity information in view of biological and/or behavioral tracking and/or external conditions.

BACKGROUND OF THE INVENTION

Despite advances in many areas of technology, there are still barriers to assessing the relative health of a person in a rapid, cost effective, and timely manner. With the increase in health care costs and prevalence of diseases related to unhealthy lifestyles such as diabetes and heart disease, it is important to assess the relative health of individuals, and this has not been adequately addressed. Moreover, in many areas of the world access to doctors is limited. Even in the developed world, a doctor's time is considered a precious commodity and there are often long waiting lists and doctor-to-specialist referral systems that have to be navigated before being seen. Accordingly, it can be very difficult to gain access to medical professionals in order to receive information about one's health.

Over recent years, fitness tracking devices have been employed to monitor the health and activity of individuals. Devices for biological and physiological monitoring, such as for blood pressure, heartrate and temperature, can communicate via Bluetooth or other wireless protocol to a computing device. Behavioral and activity monitoring can also be provided via one or more devices, such as pedometers and other accelerometer-based devices, which can also send signals representing fitness activity of an individual wirelessly to one or more computing devices. Moreover, hardware has been integrated and implemented in communication devices, such as smart phones, and used in tracking user activity, as well as biological and physiological information. Unfortunately, such tracking devices operate in an isolated fashion and do not collectively contribute to provide an accurate and timely representation of a person's biological, physiological and/or activity-based conditions.

More recently, mobile apps have been developed that integrate signals received from various fitness tracking devices. Exercise goals can be defined by users of such apps, and as a user exercises, the user can be informed of how well he or she is doing to meet such goals. For example, active diaries (e.g., provided by "Moves" app) can record walking, cycling, running and other activity, and also present reports for users regarding distance, duration, number of steps taken and number of calories burned for respective activities.

Despite recent advances in fitness tracking technology, fitness activity continues to be represented in misleading ways and requires user input and manual intervention to correct for inaccuracy.

SUMMARY

It is with respect to these and other considerations that the present application is presented.

In one or more implementations, the present application includes a system and method to classify user activity. A passive tracking device, a processor configured to receive information from the tracking device, and a database are disclosed, in which the database is accessible by the processor and stores tracking device information, user profile information and external information. The processor is configured to execute instructions that cause the processor to perform various steps, such as to define a first activity unit having a first start time that corresponds to detection of the user being engaged in an activity, and monitor the tracking device information, the external information or both. The processor is further configured to establish a first end time of the first activity unit using the monitored information, and automatically ascribe a classification of the first activity unit. The classification of the first activity unit is output to a display of a computing device, and the classification of the first activity unit is stored in the database.

Moreover, a user interface is provided that includes selectable options associated with the first activity unit. Thereafter, in response to at least a received selection of at least one of the selectable options, the classification is revised by: joining the first activity unit and a second activity unit having a second start time and a second end time, such that the revised classification has a start time equal to the first start time and an end time equal to the second end time. Further, the first activity unit is merged with a second activity unit having a second start time and a second end time, such that the revised classification has a start time equal to the first start time and an end time equal to the second end time. Alternatively, the first activity unit is divided into at least two activity units, each of at least two activity units having a different respective start time and a different respective end time. The revised classification is output to a display of a computing device, the revised classification is stored in the database.

Moreover in one or more implementations, the processor is configured to execute instructions to generate and provide an audit trail that identifies at least a difference between the classification and the revised classification. Further, the audit trail can be configured for compliance review.

Moreover in one or more implementations, the first activity unit and the second activity unit can be minor activity units, and joining the first activity unit and the second activity unit comprises including both the first activity unit and the second activity unit into a major activity unit.

Furthermore, in one or more implementations, the first activity unit and the second activity unit can be minor activity units, and merging the first activity unit and the second activity unit comprises reducing the number of activity units to one minor activity unit that comprises the first activity unit and the second activity unit.

Moreover in one or more implementations, the tracking device information includes at least one of biological information and geolocation information. Further, the user profile information can include demographic information associated with at least one user. Yet further, the external information can include at least one of schedule information, calendar information and weather information.

Moreover in one or more implementations, the processor is configured to execute instructions that cause the processor to define, as a function of a first portion of the tracking information, a baseline representing a condition of a person who is not engaged in activity. The detection of the user being engaged in an activity can be based at least in part on a detection in a change from the baseline.

BRIEF DESCRIPTION OF THE DRAWING FIGURES

Various features, aspects and advantages of the invention can be appreciated from the following detailed description and the accompanying drawing figures, in which:

FIG. 1 a diagram of an example hardware arrangement in accordance with an example implementation;

FIGS. 4A and 4B illustrate example screen displays, associated with entering data, associated with activity;

DETAILED DESCRIPTION OF THE EMBODIMENTS

Figure 1:
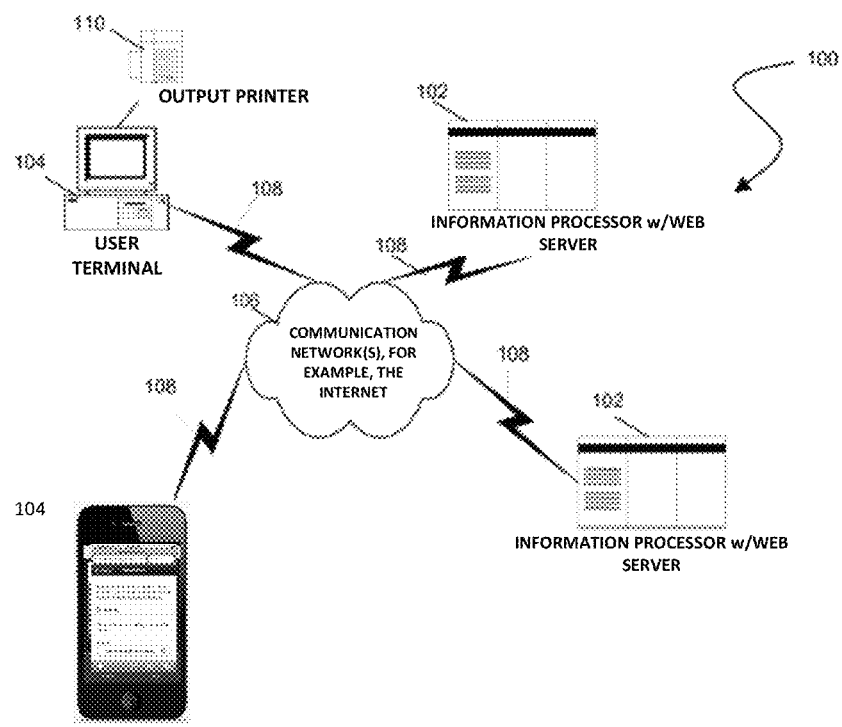

By way of overview and introduction, the present application provides an improved system and method for integrating information received from a plurality of distinct tracking devices with historical and behavioral information associated with user activity and health. A sophisticated, machine-learning health and activity classification engine is provided that analyzes information received from various sources, including fitness tracking devices, to classify a user's activity and health. Information representing individual activity units can be flexibly joined together to represent specific activity in a new and accurate way. Moreover, the present application provides a predictive element that, beyond simply determining specific activity that a user may be engaged in, defines activity goals that are modified over time to encourage and press users to adapt to more strenuous (or less strenuous) exercise regimen.

In one or more implementations, the classification engine is provided with a sequential and/or continuous stream of user information that is passively tracked. Such information can include sensor data from various sources, such as a pulse monitoring device, one or more accelerometer-related applications (e.g., a pedometer or other motion detecting application), a temperature sensing device, a pulse oximeter and/or a global positioning system ("GPS") device. In addition to such sensor data, user profile information is accessed and/or managed that represents, for example, a user's age, gender, height and weight, as well as various biological and/or physiological characteristics that are particular to an individual. One more modules can aggregate such user profile information to provide demographic information and to function as predictive mechanisms. Moreover, other sources of information can be accessed or otherwise managed by the classification engine that contribute to determining and/or predicting various forms of user activity and health. For example, calendar information for a user's personal and/or professional schedule can be accessed and managed by the classification engine. Such calendar information can include workout schedules, personal schedules, work schedules or virtually any other calendar entry. In addition, the classification engine can access and process various external data sets, such as time of day, as well as specific day, week and month information, including local weather, in order to classify and predict user activity and health.

Thus, information from various sources, including sensors, user profile databases and calendar-related information can be managed and processed. Activity patterns can be recognized and used to predict and classify specific activity that a person may be engaged in. Moreover, as a person engages in respective activity, such as regular workouts, a determination module can determine that the user has reached a plateau and should be engaged in more strenuous and/or vigorous activities. As a person physically develops as a result of engaging in various and regular exercise, that person's tolerance improves and the effectiveness of the initial exercise regimen reduces. Thus, one aspect of the classification engine is to detect when a person is ready to advance further in his or her exercise regimen and to coach the user accordingly.

In one or more implementations of the present application, a user's heartrate can be periodically or continuously detected and monitored. A baseline heartrate and/or a calculated MET value, can be established as a function of such monitoring, and any detected heartrate within a respective range (e.g., between 65 and 75 bpm) can be used to form a determination that a user is at rest. At another point in time when the user's heartrate is elevated, such as to 105 bpm, a determination can be made that the user is performing some activity. Upon detection of the change in heartrate, one or more algorithms can be executed by a computing device and the respective activity can be automatically determined and classified, in accordance with the teachings herein, to define an activity unit having a start time, an end time, and an activity name. In other implementations, activity units can be defined based on other information sources provided to the classification engine, such as location information.

Referring now to the drawings figures in which like reference numerals refer to like elements, With reference now to FIG. 1 a diagram of an example hardware arrangement is shown that operates for providing the systems and methods disclosed herein, and designated generally as health platform 100. Health platform 100 is preferably comprised of one or more information processors 102 coupled to one or more user computing devices 104 across communication network 106. User computing devices may include, for example, mobile computing devices such as tablet computing devices, smartphones, personal digital assistants or the like. Further, a plurality of sensing devices can be included that transmit various health-related information to computing devices.

Information processor 102 preferably includes all necessary databases for the present application, including image files, metadata and other information relating to artwork, artists, and galleries. However, it is contemplated that information processor 102 can access any required databases via communication network 106 or any other communication network to which information processor 102 has access. Information processor 102 can communicate devices comprising databases using any known communication method, including a direct serial, parallel, USB interface, or via a local or wide area network.

Figure 2:
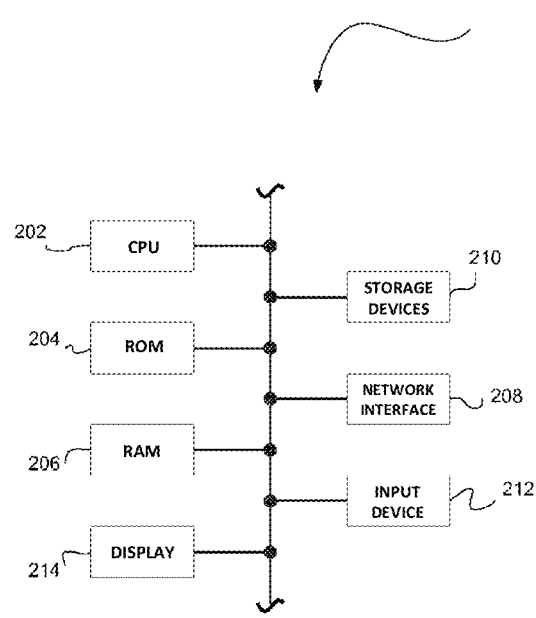
FIG. 2 illustrates functional elements of an example information processor and/or workstation in accordance with an implementation of the present application.

As shown in FIG. 2 the functional elements of each information processor 102 or workstation 104, and preferably include one or more central processing units (CPU) 202 used to execute software code in order to control the operation of information processor 102, read only memory (ROM) 204, random access memory (RAM) 206, one or more network interfaces 208 to transmit and receive data to and from other computing devices across a communication network, storage devices 210 such as a hard disk drive, flash memory, CD-ROM or DVD drive for storing program code, databases and application code, one or more input devices 212 such as a keyboard, mouse, track ball and the like, and a display 214.

The various components of information processor 102 need not be physically contained within the same chassis or even located in a single location. For example, as explained above with respect to databases which can reside on storage device 210, storage device 210 may be located at a site which is remote from the remaining elements of information processors 102, and may even be connected to CPU 202 across communication network 106 via network interface 208.

The functional elements shown in FIG. 2 (designated by reference numbers 202-214) are preferably the same categories of functional elements preferably present in user computing device 104. However, not all elements need be present, for example, storage devices in the case of PDAs, and the capacities of the various elements are arranged to accommodate expected user demand. For example, CPU 202 in user computing device 104 may be of a smaller capacity than CPU 202 as present in information processor 102. Similarly, it is likely that information processor 102 will include storage devices 210 of a much higher capacity than storage devices 210 present in workstation 104. Of course, one of ordinary skill in the art will understand that the capacities of the functional elements can be adjusted as needed.

Figure 3:
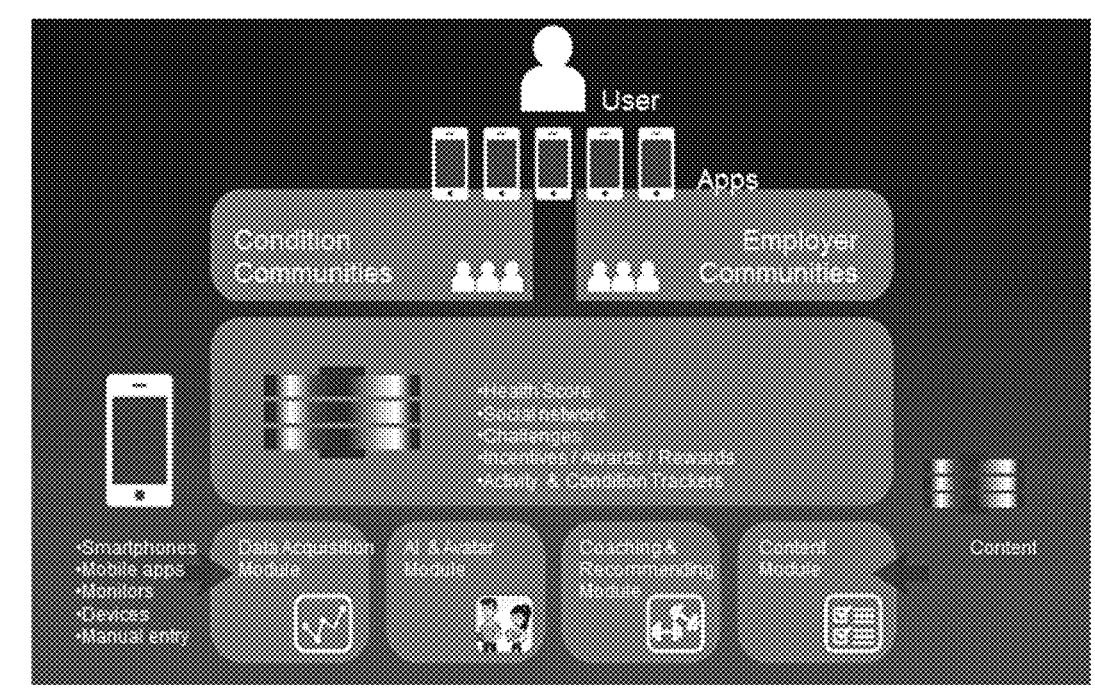
FIG. 3 is a block diagram that illustrates functional building blocks associated with a health platform, including for calculating a health score, in accordance with an example implementation.

FIG. 3 is a block diagram that illustrates functional building blocks 300 associated with a health platform, including for calculating a health score, as well as implementing many of the features shown and described herein. The health platform system in accordance with the present application can be accessed via Internet web browser software applications (e.g., CHROME, FIREFOX, SAFARI, INTERNET EXPLORER), and by using a desktop or laptop computer as well as from a mobile device, such as a Smartphone or Tablet via a mobile optimized version of the web site.

Figure 4A:
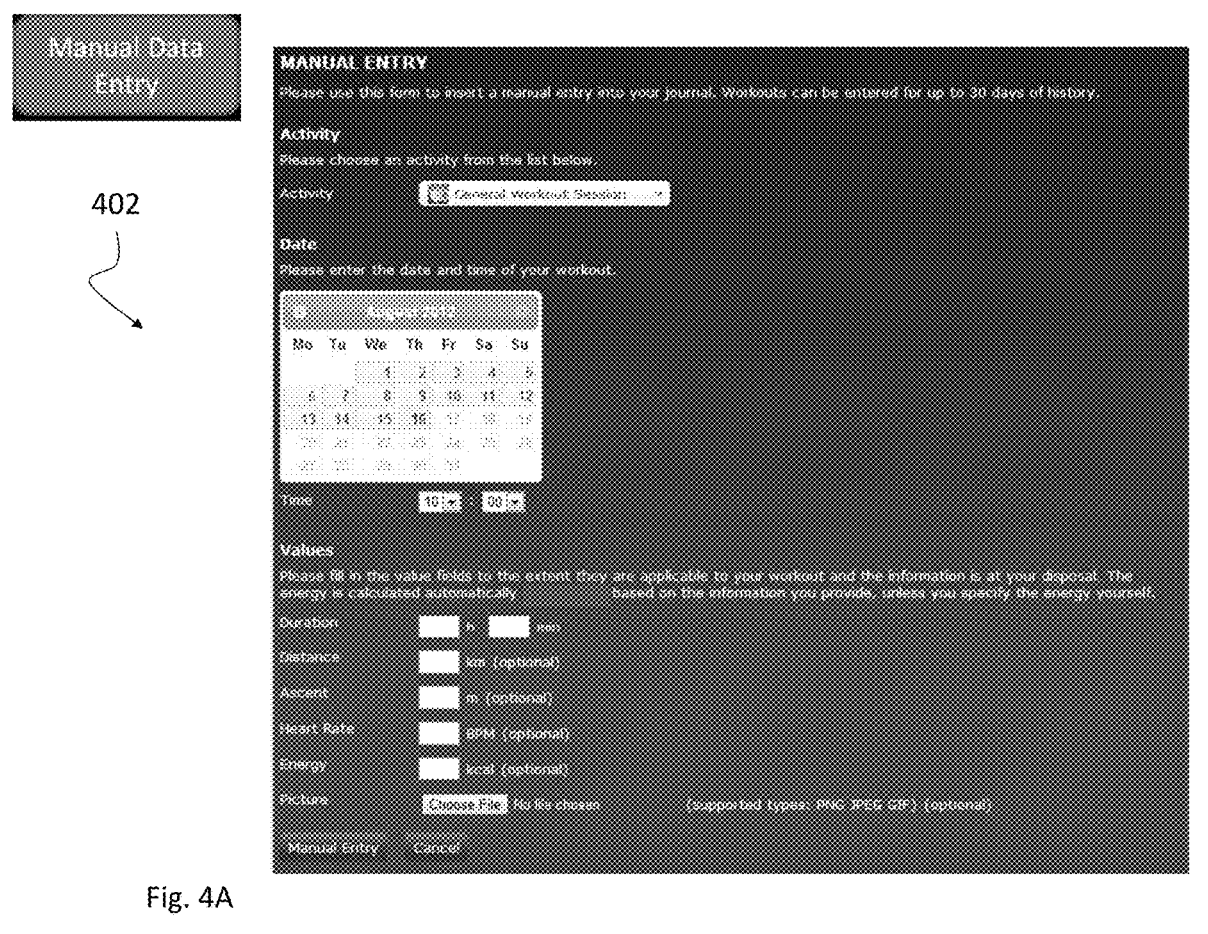
Figure 4B:
Figure 4B:
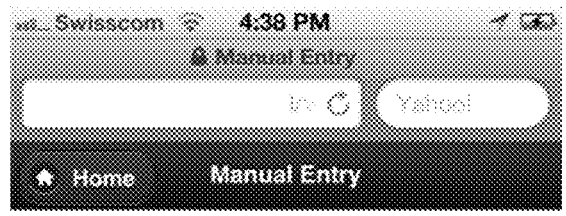
Figure 4B:

FIGS. 4A and 4B illustrate example screen displays 402 and 404, associated with entering data, e.g., via a graphical user interface via screen controls (e.g., buttons, icons, drop-down lists, radio buttons, checkboxes, textboxes or the like) and submitted by the user. As shown in FIGS. 4A and 4B, information, such as relating to indoor and outdoor activity can be inserted manually via a web form or via a mobile platform and users can also choose to upload images together the information associated with their activity. Alternatively (or in addition), data entry can occur substantially automatically, such as via an import process of one or more files formatted in one of various file types (e.g., TXT, DOC, PNG, JPEG, GIF, GPX, and TCX).

The health platform can be configured with a smartphone software application, referred to herein generally, as a "tracker application," to track fitness activities in an easy and automatic way (in addition to providing for manual entry) and the recorded/tracked activities can be uploaded automatically on the health platform. The tracker application can be provided for devices operating IOS, Android and BlackBerry operating systems, and can be provided at no charge to the user. For example, workout data can be uploaded via the tracker application.

In one or more implementations, the present application offers the tracker application to track a user's fitness activity, and can be implemented on devices running IOS, ANDROID, WINDOWS PHONE, BLACKBERRY and other suitable mobile device operating systems. Outdoor and indoor activities can be tracked, and data upload to a server computer or other device can be provided in a secure format. The data can be seamlessly and automatically integrated for calculating a user's health score. For example, daily activity measured by step counters/pedometers or other similar devices can be integrated using the systems and methods shown and described herein. An example and non-exhaustive list of activities provided via the tracker application and usable to calculate a user's health score is illustrated in an example display screen 500 in FIG. 5.

Moreover, in one or more implementations, an interactive interface, such as an avatar is supported for interacting with a user, including to encourage the user to provide health-related information, such as by functioning as a coach. Generally, notifications can include questionnaires or prompts for information, and can be presented by the avatar.

Figure 6:
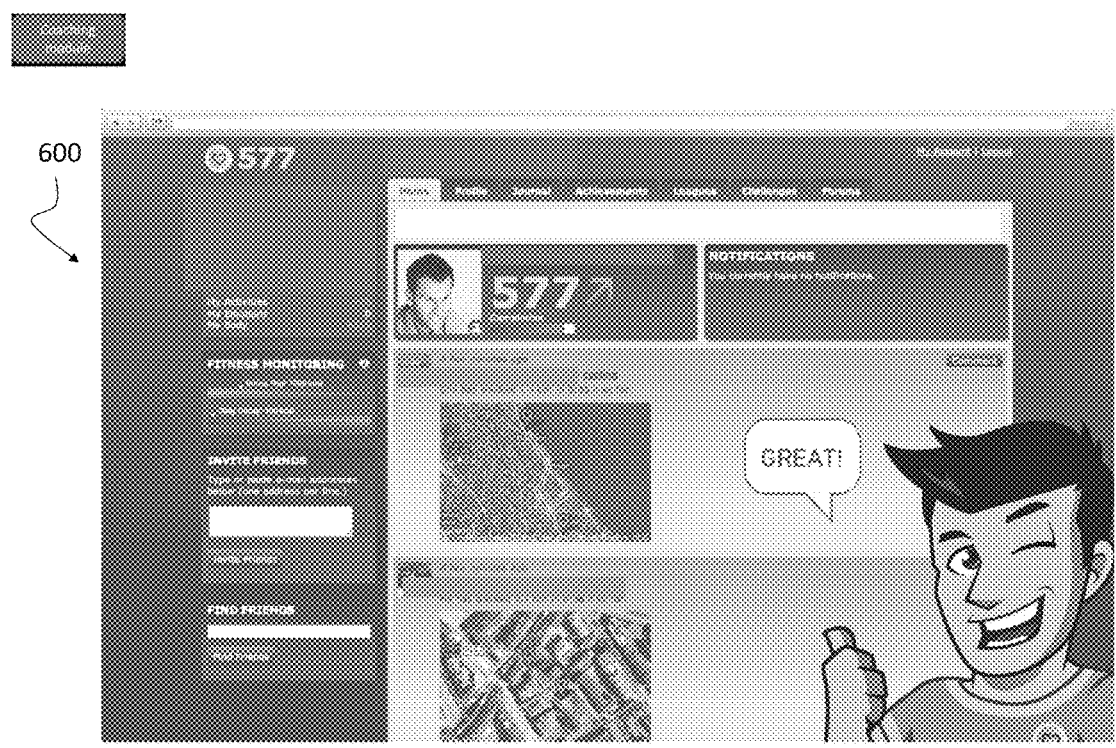
FIG. 6 is an example display screen that illustrates a determination of user activity as a function of a user's heartrate, in accordance with an example implementation of the present application.

An example is shown in FIG. 6. While appearing as a relatively simple interface, the avatar can operate in complex interactive ways, including by accessing databases and providing responses to user queries, substantially in real-time.

As noted above, the present application can be configured to provide representations of "minor" activity units that are classified in a respective "major" activity unit. Moreover, as a user engages in an exercise regimen, one or more activity goals can be defined that are modified over time to encourage and press users to engage in more strenuous activity. In one or more implementations, an avatar or other interactive interface can prompt the user to adjust a major activity unit in an effort to recommend engaging in an exercise activity that may require additional effort or energy. Upon receiving an indication that the user is agreeable, the present application can dynamically adjust the minor activity units, such as the length of time for performing one or more of the activity units, or increasing an adjustable setting associated with particular equipment (e.g., a resistance of a treadmill). Thus, the present application can be configured to monitor and classify respective activity and adjust such activity in one or more ways to increase exercise regimens and improve health.

In addition to a baseline calculated health score, the present application includes one or more modules that provide a form of a health score screener that can provide health score values that go beyond the individual person level. Providing health-related information associated with a population in a concise, anonymous and meaningful format can aid many industries and technologies. For example, insurance companies can use population-based health scores for risk modeling, and can assist employers to reduce their premiums and improve the health of their employees by identifying specific at-risk populations. Populations can be defined in countless ways, including by geography, by socio-economic demographic, by gender and by occupation, to name but a few. Health-related information, including population-based health scores, can identify a return on investment ("ROI") and associated costs resulting inaction.

In a broad aspect, a method according to the invention can be understood as collecting health related information, processing the information into a health score, and publishing the health score is provided. A system for implementing the method can include a computer having, a processor, memory, and code modules executing in the processor for the collection, processing, and publishing of the information. Baseline information can be determined and provided in response to relatively little and initially received responses from a user, which can engage the user in the future. Further, population health score information can be provided, including as a function of demographics. In addition, changes in heartrate information can be detected, and used to determine (including automatically) respective activity of a user.

In one or more implementations, a daily, substantially real-time calculated health score is provided and is integrated in connection with a feedback loop and artificial intelligence (e.g., avatar) that enables users to learn about their health and lifestyles. The health score can be provided with content in connection with activity tracking, sleep monitoring and/or stress exposure. In connection with activity monitoring, a user's heartrate and/or calculated MET can be based on information detected by breast heart bands, smart watches, soft sensors, contact devices, nano sensors, and/or other suitable technology.

Moreover, one or more goals and/or challenges can be tailored for individuals' lifestyles. The result can be a relevant, easy and fun factor that represents a degree in which a user and/or members of an organization are involved with maintaining good health in accordance with the teachings herein. Moreover, a reporting module can be provided for individuals and/or various groups of persons, such as company departments, profit centers, entire companies, and even regionally (e.g., over one or more countries). The result is significant cost savings attributed to healthcare.

In non-limiting use, a passive tracking device can include a one or more passive tracking devices. Also in non-limiting use, a processor can include one or more processors. Still further in non-limiting use, a database can include one or more databases.

Figure 5:
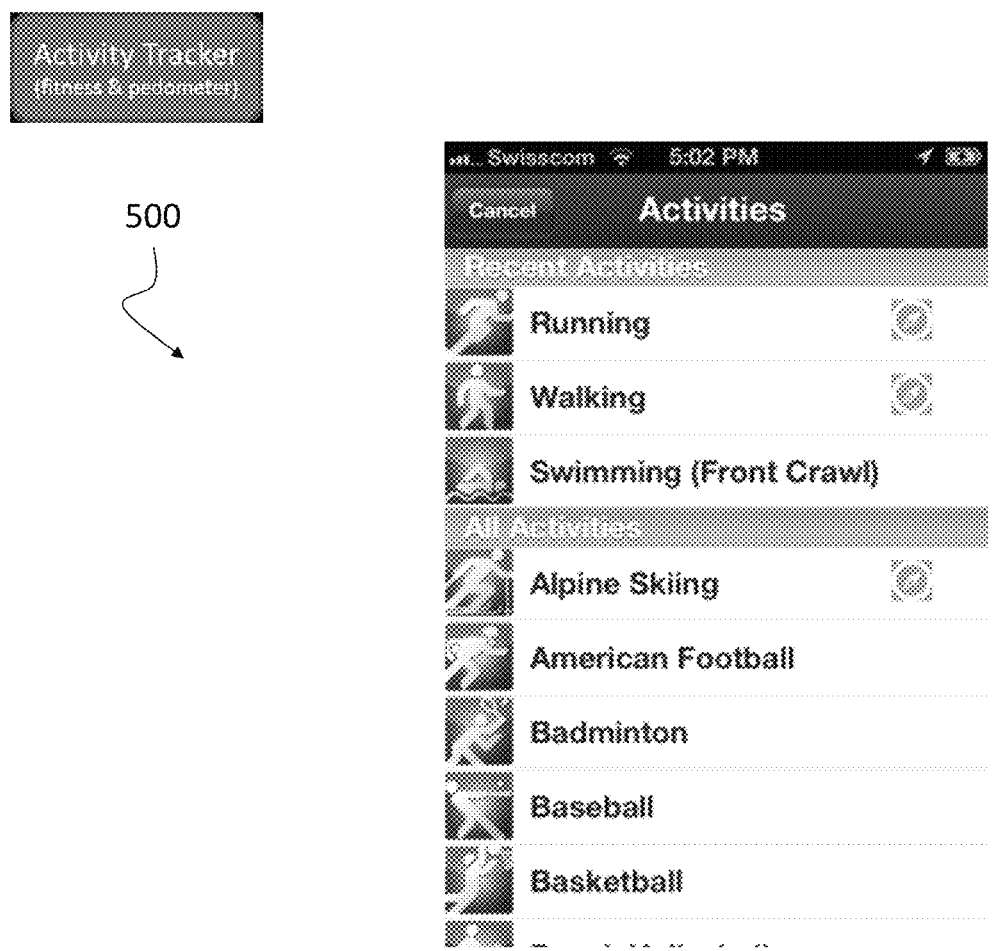
FIG. 5 illustrates a non-exhaustive list of user activities.
Figure 7:
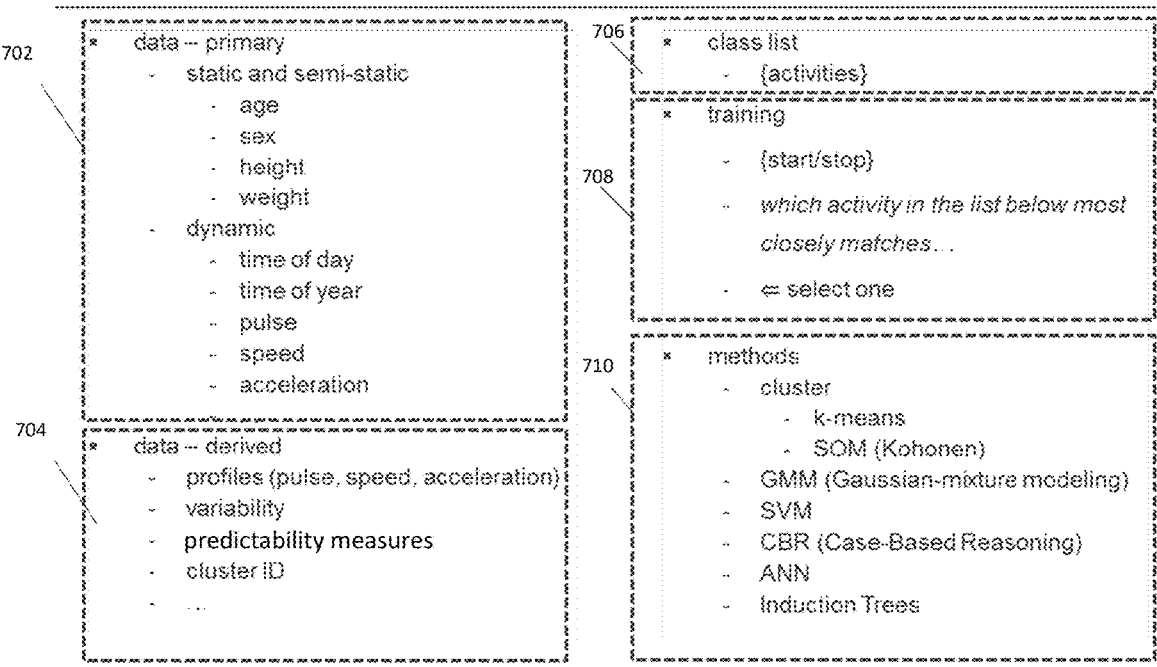
FIG. 7 is a block diagram illustrating components associated with a self-learning activity identification system.

FIG. 7 is a block diagram illustrating components associated with a self-learning activity identification system 700, in accordance with an implementation of the present application. As illustrated in FIG. 7, primary data 702 can include, for example, static and semi-static values associated with a user's age, gender, height and weight. Dynamic primary data can include dynamic values that are sensed or detected, such as time of day, time of year, heartrate (pulse) speed and acceleration. Derived data values 704 can include profiles associated with heartrate, speed and acceleration, variability, predictability measures and cluster ID. Activity class list 706 represents, for example, activities that a user can be engaged in and is usable by the classification engine to determine and classify activity that is detected as a function of biological and/or physiological values, e.g., pulse rate, temperature, blood pressure or the like. Examples of user activities can include, for example, running, walking, swimming or engaging in various sports (FIG. 5). In one or more implementations of the present application, the classification engine can be trained, such as for future classification of activity. For example, training section 708 identifies starting and stopping training operations, and enabling selectable options for users to identify respective activity that may have occurred or be occurring. Machine learning methods 710 can include cluster-based learning, such as for pattern recognition (e.g., K-Mean clustering, self-organizing mapping (SOM, Kohonen), Gaussian-Mixture Modeling (GMM), Support Vector Machine (SVM), Case-Based Reasoning (CBR), ANN, and Induction Trees).

Figure 8:
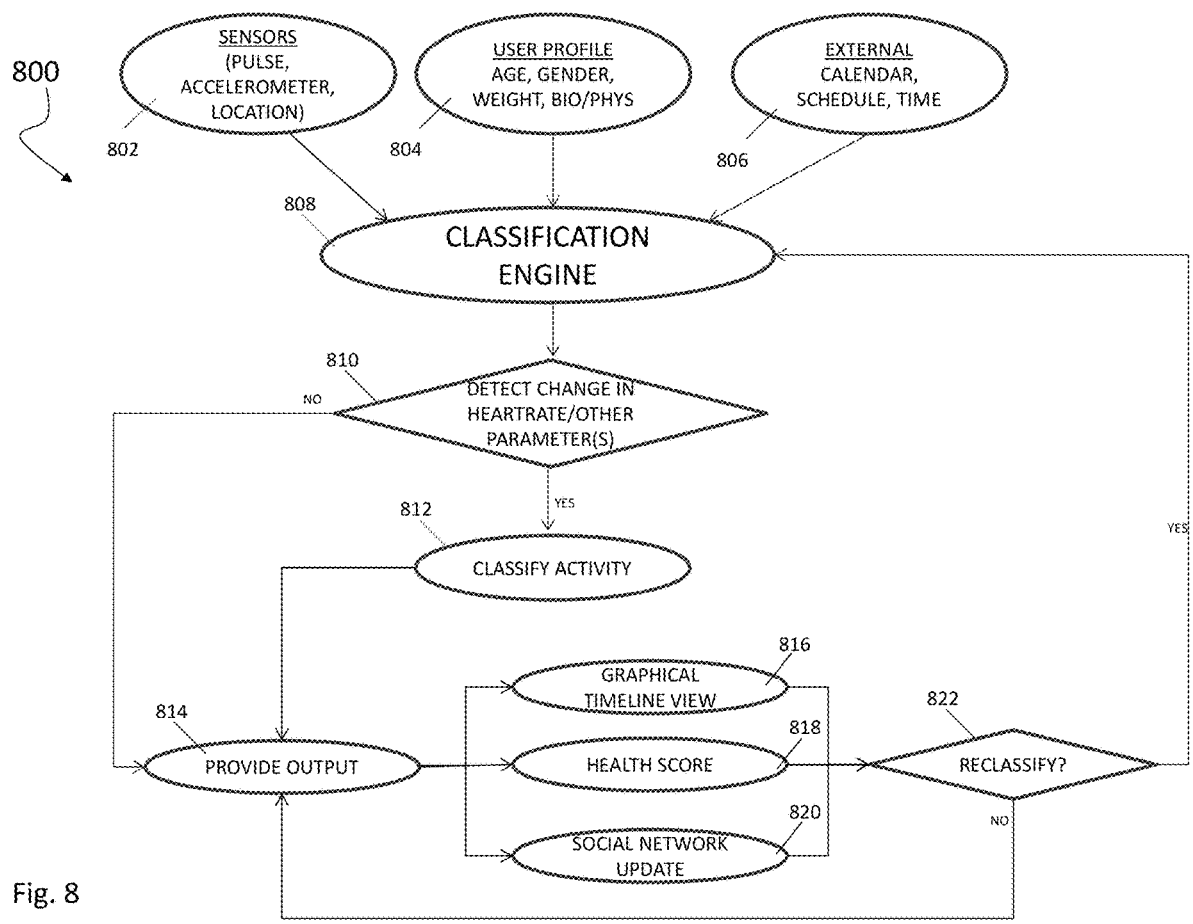
FIG. 8 illustrates an example flow of information and steps associated with a self-learning activity identification system in accordance with one or more implementations of the application.

FIG. 8 illustrates an example flow of information and steps associated with a self-learning activity identification system in accordance with one or more implementations of the application. Sensor information 802, user profile information 804 and external information 806 can be transmitted to or otherwise accessed by classification engine 808. At step 810, a change is detected, for example, in the user's heartrate, respiratory rate or other parameter. As noted above, a user's heartrate while at rest can be established as a parameter, and as sensed information is obtained by one or more processors that the user's heartrate has exceeded the at rest parameter, a determination can be made that some user activity, such as exercise, is occurring. Thereafter, the activity is classified as specific activity, such as a function of one or more machine learning methods 710 (812), with a start time and, eventually, after detection of the conclusion of the activity, an end time. It should be appreciated that when one activity ends, another, in theory, begins, if only an "at rest" activity. Whether the activity conclusion and start have been correctly discerned by the algorithm or established is a facet of one or more implementations of the present application.

The step of classifying activity is not trivial and can be the result of complex processing of dynamic information received from a plurality of sensing devices with profile and external data that are accessible to one or more computing devices. For example, using GPS and calendar information, one or more machine learning techniques detect a pattern that a user goes to the gym between the hours of 4:00-5:00 p.m. on Sundays. The user may also provide information via a feedback loop (shown and described herein) that the user enjoys body pump (weightlifting) activity most, and is engaged in body pump challenges with other users. Upon a detection of a change in heartrate from the baseline condition, available signals from tracking devices now known or later developed can be processed to classify the respective activity that the user is engaged in. In another example, user profile information may represent that a user engages in skiing activity and sailing activity. Using various forms of dynamic and external information, detected activity can be classified correctly. For example, a computing device would be incorrectly classifying user activity as sailing in view of GPS coordinates that identify that the user located on top of a mountain, and in view of calendar information that represents that it is wintertime, and further in view of weather information that represents it is snowing where the user is located. Such activity, in view of all of the relevant composited information and associated with the user's elevated heartrate would correctly classify the activity as skiing. Moreover, monitoring heartrate information (and other physiological and metabolic-based information) enables a period of time for which activity is occurring.

Thus, the present application provides sophisticated processing of activity-based information to classify an activity accurately. This can be the result of processing specific and discrete periods of time and various information shown and described herein. For example, discrete determinations represent that a user is very active for five minutes, relatively inactive for the next two minutes, and active again for the following five minutes could result in three activity units being defined, or three minor units of a major activity unit; each having respective begin and end times. Location-based information over the course of the same 12 minutes represents that the user traveled five miles. An inaccurate classification of activity would be that the user walked briskly to a bus stop, rode a bus for 4-5 miles, got off the bus and continued walking briskly. However the present application correctly classifies the user's activity as riding a bicycle and the periods of strenuous activity represent peddling uphill, the period of relative inactivity represent coasting downhill. The automated classification engine in accordance with the present application analyzes not just one or two data points, but provides for a holistic and complex processing of many sources of information, including extrinsic activity such as time of day, day of week, location and weather, to correctly classify activity. For example, the same 12 minutes activity information that are identified to have occurred late at night and in the winter during a heavy snowfall would not result in a classification of bicycle riding. This represents the complex arrangements and collaborative-based system of respective hardware and software devices that contribute to an analysis of discrete portions of activity over time for improved and accurate classification of such activity.

In addition to providing automatic classifications of user activity, the present application provides for fault tolerance and provides users with an ability to reclassify activity. In one or more implementations, a user interface is provided that includes interactive and selectable elements that represent user activity over time (e.g., a graphical representation of a timeline). For example, a timeline is generated and displayed that identifies when a user woke, a period of time, distance and number of steps taken before getting in a car, the distance and time spent while in motorized transit, the distance, period of time, and number of steps while running, a period of time in which the user is thereafter dormant (e.g., sitting behind a desk), the amount of food consumed during lunch, a period of time, distance and number of steps taken during an afternoon run, a period of time in which the user is again dormant (e.g., sitting behind the desk), and a period of time and type of activity after the user left work (e.g., 15 minutes of bicycle riding for five miles). In one or more implementations, each of the respective timeline entries comprises a flexible activity unit which is selectable and the user can take corrective action, such as to reclassify the activity, merge several activity units, revise the amount of time during the activity or revise any other data element associated therewith. Each time a reclassification or other revision is made, such information is preferably provided back to the classification engine for further learning. Optionally, changes to activity unit labels, duration, and joinder to other activity units can be included in an audit trail for reporting and compliance review purposes.

Figure 9:
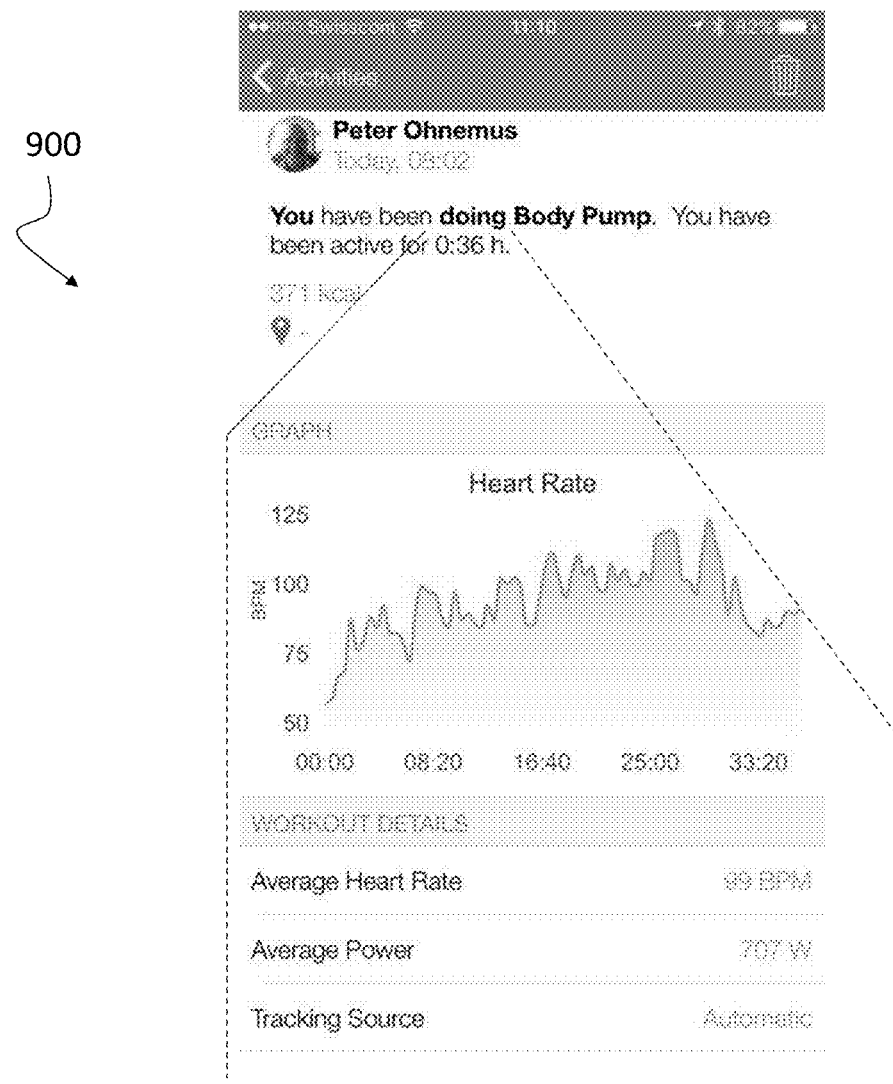
FIG. 9 is an example display screen that illustrates a determination of user activity as a function of a user's heartrate, in accordance with an example implementation of the present application.
Figure 10:
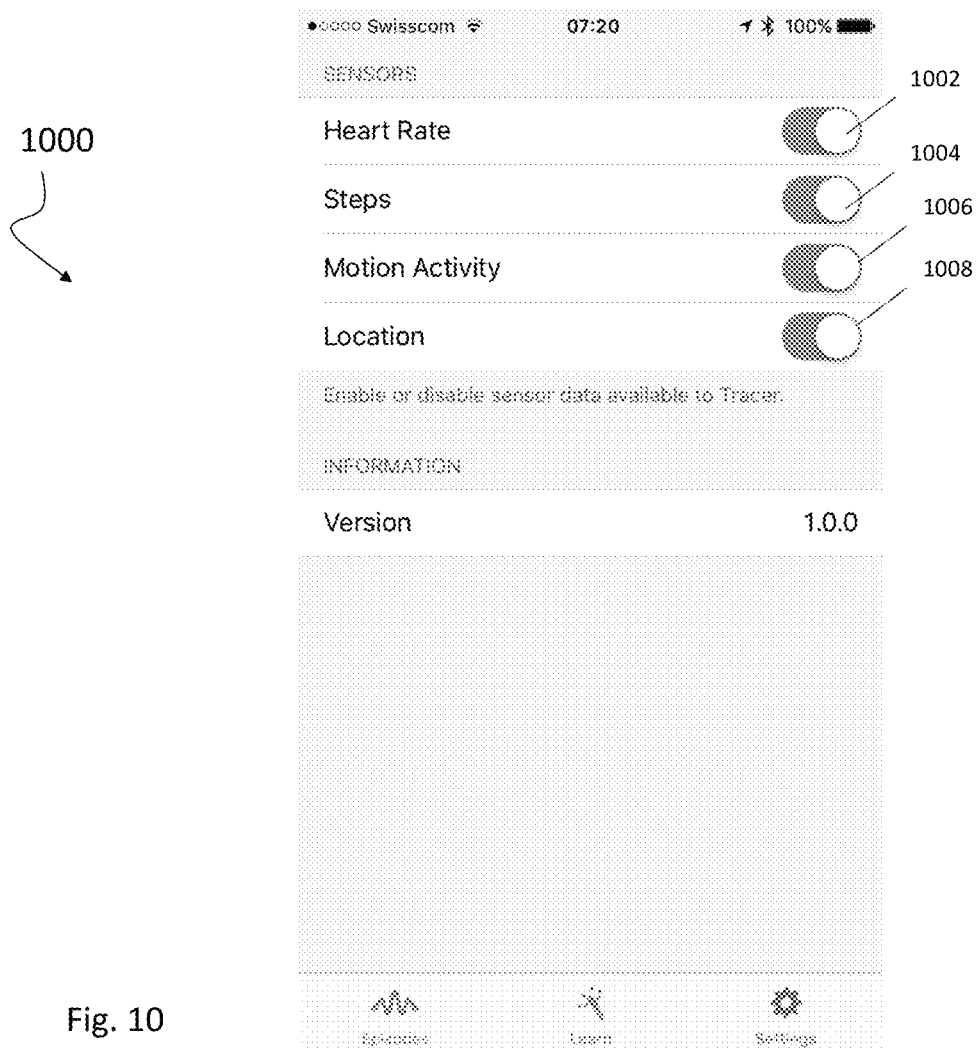
FIGS. 10-12 illustrate example data entry display screens associated with example implementation of the present application.

FIG. 9 illustrates an example display screen, such as provided on a mobile computing device (e.g., a smartphone), in which user activity has be detected substantially automatically, such as by monitoring heartrate and during a specific period of time (e.g., 0.36 h). The user's activity can be determined, for example, via machine learning in accordance with the teachings herein. The user can further, for example, be prompted to communicate with the avatar to express how the user felt during the respective activity. Other information illustrated in FIG. 9 includes a graphical display of the user's heartrate over time, as well as determinations of average heartrate, average power, and tracking source.

Continuing with reference to the process/information flow 800, at step 814 output is provided, for example, to a computing device associated with a user, that represents the classified activity. For example, a graphical representation of timeline is generated and provided (816), a user's health score (as shown and described herein) is generated and provided (818), an update is provided to one or more social networks (820) or other suitable output is provided. Thereafter, a determination is made that activity information, such as provided in a timeline, is to be reclassified (822). If so, then the process branches to 808 and information associated with the reclassified entry is provided back to the classification engine. Alternatively, if the determination in 822 is that no reclassification is needed, then the process branches back to step 814 and output is provided.

In one or more implementations, individual activity units representing discrete periods of activity are classified automatically by a computing device in accordance with information processed by the health and activity classification engine. For example, a user at a gym spends 10 minutes in body pump activity, and raises his heartrate to 110 bpm. After a few moments, the user's heartrate returns to an at-rest state (e.g., 70 bpm). In this example, the determination that the heartrate has resumed an at-rest state signifies the end of the discrete activity unit. Thereafter, the user spends 5 minutes on a treadmill, and raises his heartrate again to 105 bpm, thereby signifying to the computing device another discrete activity unit. Thereafter, the user spends 5 minutes on a stationary bicycle, which is interpreted as a third discrete activity unit. Each of these activity units can be joined into a major activity unit, e.g., "gym workout" which has an overall duration that spans the beginning of the body pump activity through the end of the treadmill activity. This joinder is different than a merge, which is an alternative way of reducing the number of activity units by combining two or more units.

The benefit of the present application is that activity units are provided in a flexible format that enable users to reclassify activity units, as well as to combine a plurality of activity units into a unified group, such as a plurality of "minor" activity units into a single "major" activity unit or merge two or more units into a single major or minor unit. Continuing with the previous example, the user reviews a timeline of activity that occurred while the user was at the gym. Upon detecting three respective activity units (body pump, treadmill and stationary bicycle) the user makes selections, via one or more graphical screen controls provided in the user interface, to classify the plurality of activity units into a single activity unit: "gym workout." Thus, minor activity units can be classified as part of a single major activity unit, in accordance with the present application. Similarly, options can be provided for user to parse a single activity unit into a plurality of activity units. As activity is reclassified, including into single (major) or multiple (minor) units, information is provided back to the classification engine and used for future classifying of user activity, as well as for audit purposes.

While many of the descriptions set forth in here identify changes in a user's heartrate to trigger a determination of specific user activity, the application is not so limited. As described herein, the classification engine is configured to access or otherwise receive information from sensors, individuals as well as external sources. Any one or combination of information sources can be used as a triggering by the classification engine for detecting and/or classifying respective user activity. For example, information from a GPS device and calendar source can be processed to determine that a user has arrived at a gym at a certain time of day and on a certain day of the week. This combination of data points can be used to demarcate a major activity unit: gym workout. While the user engages in various exercise activities, such as body pumping, stationary bicycling and running on a treadmill, the classification engine can define minor activity units associated with each, and can generate and provide one or more summaries representing specific activity, the duration of such activity, a graphical representation of the user's heartrate during such activity over the duration, or the like. Thus, the classification engine can be used to classify broadly a plurality of activities into a single major activity unit, while maintaining and providing information on each of the respective minor activities comprising the major unit.

In one or more example implementations, the present application provides a computer-implemented system and method configured to acquire health-related and/or medical-related data, and to process the data. For example, the systems and methods herein provide for providing feedback substantially in real-time via an on-line and/or mobile platform. Using the systems and methods disclosed herein, information can be received from user devices, and the information can be processed to provide various form of feedback, such as alerts and notifications. Upon accessing one or more modules associated with the present application, such as by a user submitting initial registration information, a baseline assessment in the form of a health score can be calculated and provided to a user at no or nominal charge. This results in engaging users with valuable health-related information and increases the likelihood that users will remain engaged and regularly provide health-related information that can be used in connection, for example, with a metric health model score and/or a quality of life model score.

In one or more implementations, the baseline assessment (e.g., the health score) is based on four data points: Age, Height, Gender and Weight (ex. Instant Health Score). In one or more implementations, a health score distribution of an organization, such as based on exciting data. A health score can be calculated across an enterprise, such as in a stateless manner, that precludes social networking, gamification or other individual identifying element.

The present application provides a distributed system in which data acquisition, data storage, and data processing can be used to produce a numerical score as a basis for assessing the relative health of a user. In an implementation, a computer-based application is provided for the collection of health-related parameters of a user and a user interface for the presentation (e.g., display) of data. The computer-based application can be implemented via a microcontroller that includes a processor, a memory and code executing therein so as to configure the processor to perform at least some of the functionality described herein. The memory can store data and instructions suitable for controlling the operation of one or more processors. An implementation of memory can include, by way of example and not limitation, a random access memory (RAM), a hard drive, or a read only memory (ROM). One of the components stored in the memory is a program. The program includes instructions that cause the processor to execute steps that implement the methods described herein. The program can be implemented as a single module or as a plurality of modules that operate in cooperation with one another. The program can include software that can be used in connection with one or more implementations of the present application.

A communication subsystem can be provided for communicating information from the microprocessor to the user interface, such as an external device (e.g., handheld unit or a computer that is connected over a network to the communication subsystem). Information can be communicated by the communication subsystem in a variety of ways including Bluetooth, Wi-Fi, Wi-Max, RF transmission, near-field communications or other suitable communication protocol. A number of different network topologies can be utilized in a conventional manner, such as wired, optical, 3G, 4G or other suitable networking protocol.

The communication subsystem can be part of a communicative electronic device including, by way of example, a smart phone or cellular telephone, a personal digital assistant (PDA), tablet computer, netbook, laptop computer, or other computing device. For instance, the communication subsystem can be directly connected through a device such as a smartphone such as an iPhone, Google Android Phone, BlackBerry, and Microsoft Windows Mobile enabled phone, or a device such as a heartrate or blood pressure monitor, weight measurement scales, exercise equipment or the like. One or more of these devices can include or otherwise interface with a module or communication unit with the subsystem to allow information and control signals to flow between the subsystem and the external user interface device. The communication sub-system can cooperate with a conventional communicative device, or can be part of a device that is dedicated to the purpose of communicating information processed by the microcontroller.

It is recognized that users can become confused regarding which respective device should be activated and when. Referred to herein, generally, as "double counting," users may inadvertently account for the same activity and/or health-related event more than once, which can result in inaccuracy and calculations that distort a user's overall health score. Moreover, some users may provide unclear or partial replies, or even intentionally distort facts. The automated processes and devices shown and described herein reduce or preclude the opportunity for users to accidentally or intentionally distort or misidentify various activity information. Moreover, audit trails can be created, as noted, to assist user's in classification and to enforce compliance.

When a communicative electronic device such as the types noted herein are used as an external user interface device, the display, processor, and memory of such devices can be used to process the health related information, such as to calculate and provide a numerical assessment. Otherwise, the system can include a display and a memory that are associated with the external device and used to support data communication in real-time or otherwise. More generally, the system includes a user interface, which can be implemented, in part, by software modules executing in the processor of the microcontroller or under control of the external device. In part, the user interface can also include an output device such as a display (e.g., the display). Display may include, for example, organic light emitting diode (OLED) displays, thin film transistor liquid crystal displays and plasma displays.

For example, one or more biosensors can be used to collect and transmit health information about a user to one or more computing devices. The biosensor can be placed in contact with or within a user's body to measure vital signs or other health-related information of the user. For example, the biosensor can be a pulse meter that can be worn by the user in contact with the user's body so that the pulse of the user can be sensed, a heartrate monitor, an electrocardiogram device, a pedometer, a blood glucose monitor or other suitable device or system. A biosensor in accordance with the present application can include a communication module (e.g., a communication subsystem) so that the biosensor can transmit sensed data, either wired or wirelessly. The biosensor can communicate the sensed data to the user interface device, which in turn communicates that information to the microcontroller. Optionally, the biosensor can directly communicate the sensed the data to the microprocessor. The use of biosensors provides a degree of reliability by eliminating user error associated with manually entered and/or self-reported data.

Moreover, one or more computing devices, including a server, a smartphone, a laptop, tablet or other computing device can send and receive electronic content to/from a health band that is worn by a user. The content may include, for example, numerical, textual, graphical, pictorial, audio and video material. Such communications may occur directly and/or indirectly, such as between the server and the health band via a mobile computing device such as a smart phone, tablet computer or other device. Alternatively, such communications may occur between the server and the health band without the use of computing device. Thus, in one or more implementations, the health band may employ hardware and software modules that collect and/or receive information, process information, and transmit information between the health band and a server and/or between the health band and a mobile device.

In addition to communications-related modules, the health band can include hardware and/or software modules that configure the health band to track various forms of biological/physiological characteristics, exercise and/or activity of the wearer. For example, the health band may be configured with one or more sensors and software that collect information relating to biological/physiological characteristics of the wearer, such as temperature, heartrate, blood pressure, perspiration or the like. In addition, the health band can be configured to detect and/or display humidity associated with user's skin surface. Humidity information is usable, for example, to detect that the user is or is getting dehydrated and should drink. Sensors can be used to directly collect health information about a user and report that information. The biosensor can be placed in contact with the user's body to measure vital signs or other health related information from the user. For example, the biosensor can be a pulse meter that is worn by the user in contact with the user's body so that the pulse of the user can be sensed, a heartrate monitor, an electrocardiogram device, a pedometer, a blood glucose monitor or one of many other devices or systems. The biosensor can include a communication module (e.g., communication subsystem) so that the biosensor can communicate, either wired or wirelessly, the sensed data. The biosensor can communicate the sensed data to the user interface device, which in turn communicates that information to the microcontroller. Optionally, the biosensor can directly communicate the sensed the data to the microprocessor. The use of biosensors provides a degree of reliability in the data reported because it eliminates user error associated with manually, self-reported data.

In one or more implementations of the present application, one or more algorithms can be implemented by the server, the mobile device and/or the health band that is based on the user's heartrate. One or more modules can detect automatically the user's average heartrate during the day and convert that into MET per day. For example, the user's heartrate is monitored over time and, thereafter, averaged. Thereafter, while the user's heartrate increases, user activity can be determined and/or detected.

The present application is further shown and described with reference to FIGS. 10-13.

As noted herein, sensors can be used to collect information and activities can be categorized based at least in part thereon. For example and with reference to the display screen 1000 shown in FIG. 10, graphical screen controls can be provided for users to enable one or more sensors. Selections can be made in a to activate and/or identify respective sensors that are active. Heart rate 1002 identifies information from a suitable device that can detect and/or store regular, intraday heart rate information, such as via APPLE WATCH. Steps 1004 identifies step count information from any suitable device that can detect and/or store regular, intraday step count information, such as via APPLE WATCH and IPHONE. Motion activity 1006 identifies motion information that can be received from a suitable device, such as IPHONE. In one or more implementations, a determination can be made to detect, for example, that a user is stationary, walking, bicycling, traveling in a vehicle, or engaged in other activity. Location 1008 identifies location information. that can be received from a suitable device, such as via an IPHONE. In one or more implementations, low-accuracy, background modes are used to reduce a drain on the battery and do not rely heavily on GPS. Such modes can include location hints from change of cell towers as well as visits to places as determined by a respective device, such as an IPHONE.

Figure 11A:
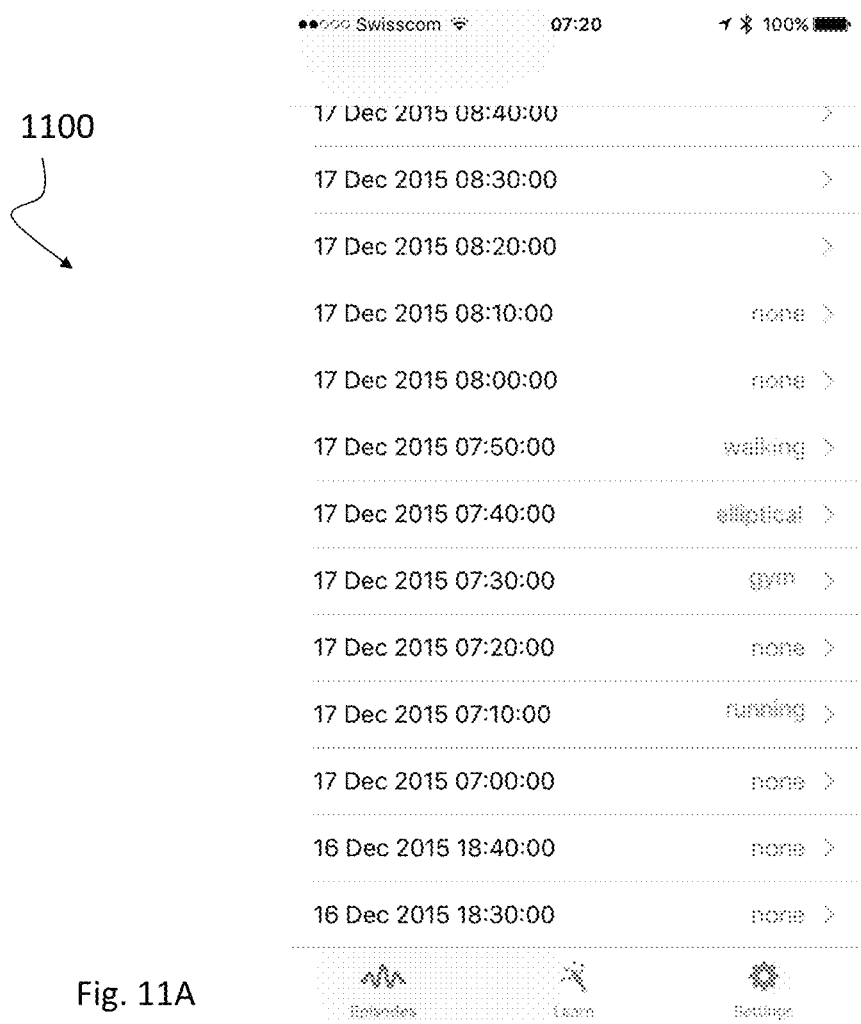
Figure 11B:
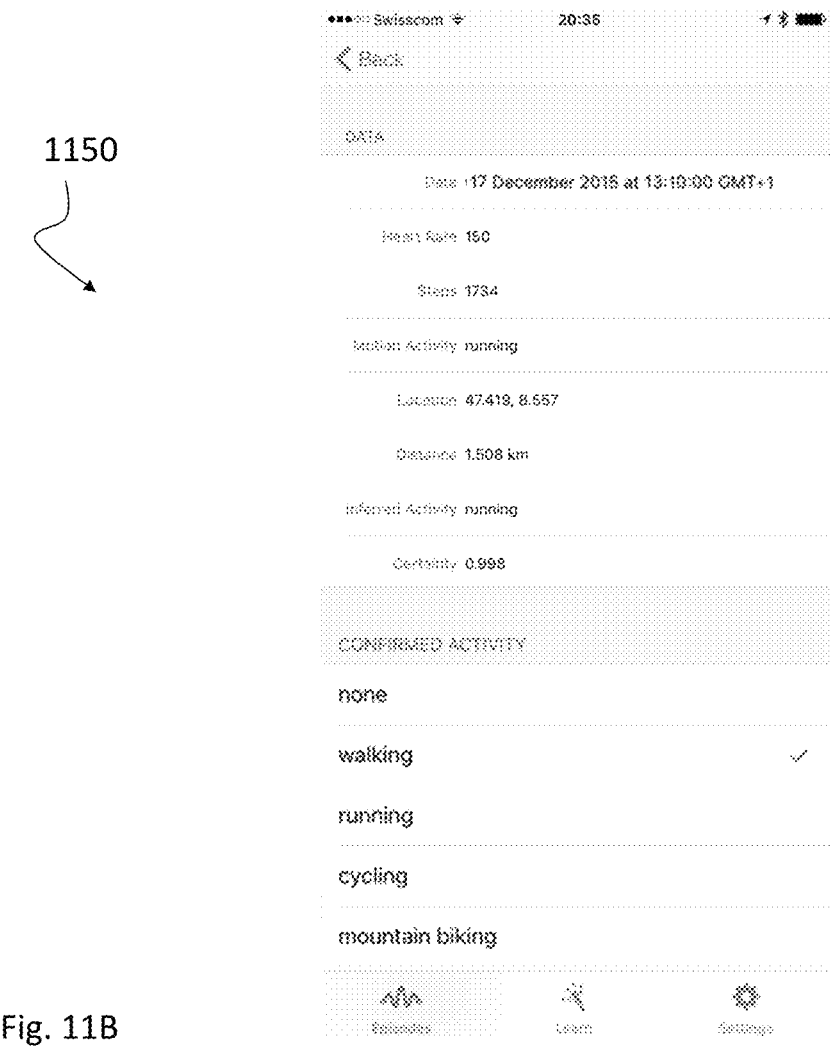
Figure 12:
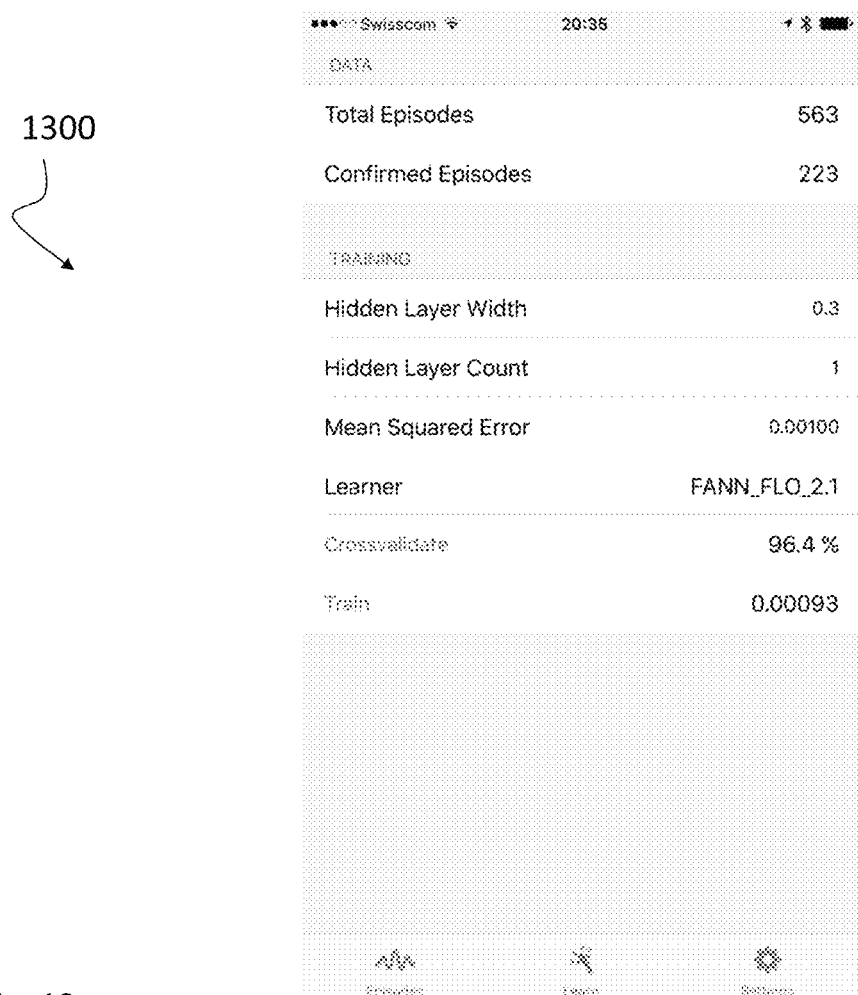

In one or more implementations of the present application, data are broken down into episodes of 10 minutes. This results in six episodes per hour, and up to 144 episodes per day. An episode may only be generated if there are heartrate data and/or step data. Recent episode data (e.g., the most recent 1,000 episodes) can be supported and shown, such as in display screens 1100 and 1150 in FIGS. 11A and 11B. As shown in FIGS. 11A and 11B, episode data can contain the following:

Date. The start of the respective episode.

Heart rate. The average heart rate during the respective episode.

Steps. The step count for the episode. In case multiple devices report step data, the app selects the device with the highest contribution for the respective episode.

Motion Activity. The motion activity for the respective episode.

Location. The coarse location for the respective episode.

Distance. The coarse distance change from the previous episode.

Inferred activity. The activity that has been statistically inferred by the trained classification model.

Certainty. A certainty of the above inference, 0 to 1.

Confirmed activity. The confirmed activity of the episode. This activity is set manually by the user and forms the ground truth for training the classification model.

In one or more implementations, users are prompted to confirm a number (e.g., 50) data associated with episodes, which are usable to train an initial classification model. Episodes are preferably confirmed for a classification model to infer such episodes in the future. For example, when a user takes a few steps inside an office building, the user confirms the episode as "none," and not as "walking," on the grounds that the user does not want such limited exercise to be categorized as a walking workout. Accordingly, the value "none" represents inactivity.

Further, the present application supports mapping terms that would otherwise have no associated meaning. For example, a user plays badminton and not tennis. In such case, the user can confirm episodes in which (s)he plays badminton by selecting a value representing tennis. In this way, exercise that occurs during badminton is recognized and accounted for.

In one or more implementations, users are prompted to confirm episodes in which activity occurs for an uninterrupted amount of time, such as 10 minutes. For example, a user goes for a walk from 14:15 to 14:45, confirms the episodes at 14:20 and 14:30 as walking, but does not confirm the episodes at 14:10 and 14:40. Such episodes are considered "dirty," and unsuitable as the ground truth for training the classification model. In such cases, users are prompted to classify the exercise as "unconfirmed." In one or more implementations, the classification model can infer activity in response to receiving several user classifications associated with a particular activity, some of which may be inconsistent, and thereafter inferring a classification based on a majority of the user-based classifications that were received.

In the event that a user unintentionally confirms an episode, one or options can be provided for the user to clear the confirmation and, thereafter, reconfirm the episode and/or confirm a future episode associated with the same activity.

After a predetermined number of episodes (e.g., 50 episodes) have been confirmed by a user, and at least 25 of which are classified as "none," the user can be prompted to further train the classification model. Options provided in an example training interface are shown in display screen 1200 in FIG. 12. The trained model can be implemented in an artificial neuronal network ("ANN"). The model is based on the up to 10,000 most recent episodes in the app, and immediately applied those episodes, including confirmed and unconfirmed ones. New episodes can be classified automatically based on the model.

Periodically, users can be prompted to re-train the model, such as when the user initially interacts with the system and/or confirms one or more episodes. In such case, a user can be prompted to review previously classified episodes and to make revisions to such classifications as appropriate. For example, users can be prompted to decide whether an inference is wrong based on the sensor data points of the episode. Users can be further prompted to determine whether more confirmed episodes for one or the other activity would increase accuracy.

Once a user has confirmed a predetermined number of episodes, such as at least 200 episodes, at least 100 of which are classified as none, the user can engage in a process to cross-validate the episodes. For example, a 10-fold cross-validation, using 90% of the confirmed episodes, can be used as a training set and the remaining 10% as test set. The process can be repeated 10 times, using a different 10% of the data as test set each time. After this cross-validation process is complete, the accuracy of the model is shown and formatted as a percentage. Occasionally, a user may repeat cross-validation steps a few times to properly gauge the accuracy, as there may be a certain degree of randomness, especially for one or more activities that have very few confirmed episodes.

In case a user sees a low accuracy (e.g., <90%), the user may want to configure hyper parameters of the ANN: One hyper parameter is a hidden layer width. The hidden layer width is relative width of the hidden layers compared to the input layer, 0 to 1. Wider hidden layers allow the algorithm to learn more complex patterns, but may lead to overfitting, thus lowering the accuracy.

Another example hyper parameter is hidden layer count. This is the number of hidden layers, 0 to 4. More hidden layers allow the algorithm to learn more complex patterns, but may also lead to overfitting, thus lowering the accuracy.

Another example hyper parameter is mean squared error. This is the stop threshold, 1 to 0.00001. Network training stops once the mean squared error over the training set has fallen below that threshold. A lower threshold allows the algorithm to train to a higher degree of precision, but, again, may lead to overfitting, thus lowering the accuracy.

After changing one or more hyper parameters, the user can re-run cross-validation one or more times to see if there is an improvement or a degradation in accuracy. When changing a mean squared error, the user may try orders of magnitude first, i.e. 1, 0.1, 0.01, . . . , 0.00001. In one more implementations, the default values of the hyper parameters can be 0.3 hidden layer width, 1 hidden layer, and 0.001 mean squared error threshold.

Although the present invention has been described in relation to particular embodiments thereof, many other variations and modifications and other uses will become apparent to those skilled in the art. It is preferred, therefore, that the present invention not be limited by the specific disclosure herein.

What is claimed:

1. A system to classify user activity, the system comprising:
    a computing device configured with a processor, non-transitory processor readable media, and instructions stored on the non-transitory processor readable media;
    a first sensing subsystem for passively tracking a physiological and/or metabolic condition of a person, the first sensing subsystem comprising a biosensor that is in contact with or within a person's body and that periodically transmits sensed information associated with the person's physiological and/or metabolic condition; and
    a second sensing subsystem for passively tracking a location of the person, the second sensing subsystem comprising a Global Positioning System ("GPS") receiver that receives GPS information that is usable to determine a location of the person;

wherein the computing device is configured to execute at least some of the instructions that cause the processor to:

receive and/or access the sensed information and information representing the determined location, classify user activity, or user health, or user activity and user health, as a function of one or more machine learning techniques;

detect a change from a respective baseline condition associated with at least some of the sensed information, and i) at least some information stored in a user profile associated with the person and ii) external information;

in response to detecting the change, the computing device is further configured to:

calculate a health score representing the user health of the person in accordance with the change from the respective baseline condition associated with at least some of the sensed information, and i) at least some information stored in a user profile associated with the person and ii) external information;

define a first activity unit having a first start time that corresponds to detection of the user being engaged in an activity;

monitor the sensed information, the external information or both;

establish a first end time of the first activity unit using the monitored information;

automatically ascribe a classification of the first activity unit;

output the classification of the first activity unit to a display;

revise the classification by:

joining or merging the first activity unit and a second activity unit having a second start time and a second end time, such that the revised classification has a start time equal to the first start time and an end time equal to the second end time; or dividing the first activity unit into at least two activity units, each of at least two activity units having a different respective start time and a different respective end time; and output the revised classification and the health score to a display of another computing device.

2. The system of claim 1, wherein the computing device is configured to execute instructions that cause the processor to:

generate and provide an audit trail that identifies at least a difference between the classification and the revised classification.

3. The system of claim 2, wherein the audit trail is configured for compliance review.

4. The system of claim 1, wherein the first activity unit and the second activity unit are minor activity units, and joining the first activity unit and the second activity unit comprises including both the first activity unit and the second activity unit into a major activity unit.

5. The system of claim 1, wherein the first activity unit and the second activity unit are minor activity units, and merging the first activity unit and the second activity unit comprises reducing the number of activity units to one minor activity unit that comprises the first activity unit and the second activity unit.

6. The system of claim 1, wherein the sensed information includes at least one of biological information and geolocation information.

7. The system of claim 1, wherein the user profile information includes demographic information associated with at least one user.

8. The system of claim 1, wherein the external information includes at least one of schedule information, calendar information and weather information.

9. The system of claim 1, wherein the computing device is configured to execute instructions that cause the processor to:

define, as a function of a first portion of the sensed information, a baseline representing a condition of a person who is not engaged in activity; and wherein the detection of the user being engaged in an activity is based at least in part on a detection in a change from the baseline.

10. A method for classifying user activity, the method comprising:

passively tracking, by a first sensing subsystem, a physiological and/or metabolic condition of a person, the first sensing subsystem comprising a biosensor that is in contact with or within a person's body and that periodically transmits sensed information associated with the person's physiological and/or metabolic condition;

passively tracking, by a second sensing subsystem, a location of the person, the second sensing subsystem comprising a Global Positioning System ("GPS") receiver that receives GPS information that is usable to determine a location of the person;

receiving, by a computing device configured with a processor, non-transitory processor readable media, and instructions stored on the non-transitory processor readable media, the sensed information from the first sensing subsystem and the second sensing subsystem;

classifying, by the computing device, user activity, or user health, or user activity and user health, as a function of one or more machine learning techniques, detecting, by the computing device, a change from a respective baseline condition associated with at least some of the sensed information, and i) at least some information stored in a user profile associated with the person and ii) external information;

in response to detecting the change:

calculating, by the computing device, a health score representing the user health of the person in accordance with the change from the respective baseline condition associated with at least some of the sensed information, and i) at least some information stored in a user profile associated with the person and ii) external information;

defining, by the computing device, a first activity unit having a first start time that corresponds to detection of the user being engaged in an activity unit;

monitoring, by the computing device, the sensed information, the external information or both;

establishing, by the computing device, a first end time of the first activity unit using the monitored information;

automatically ascribing, by the computing device, a classification of the first activity unit;

outputting, by the computing device, the classification of the first activity unit to a display;

revising, by the in response to at least a received selection of at least one of the selectable options, the classification by:
  joining or merging the first activity unit and a second activity unit having a second start time and a second end time, such that the revised classification has a start time equal to the first start time and an end time equal to the second end time;
  or
  dividing the first activity unit into at least two activity units, each of at least two activity units having a different respective start time and a different respective end time; and
outputting, by the computing device, the revised classification and the health score to a display of another computing device.

11. The method of claim 10, further comprising:
generating and providing, by the computing device, an audit trail that identifies at least a difference between the classification and the revised classification.

12. The method of claim 11, wherein the audit trail is configured for compliance review.

13. The method of claim 10, wherein the first activity unit and the second activity unit are minor activity units, and joining the first activity unit and the second activity unit comprises including both the first activity unit and the second activity unit into a major activity unit.

14. The method of claim 10, wherein the first activity unit and the second activity unit are minor activity units, and merging the first activity unit and the second activity unit comprises reducing the number of activity units to one minor activity unit that comprises the first activity unit and the second activity unit.

15. The method of claim 10, wherein the sensed information includes at least one of biological information and geolocation information.

16. The method of claim 10, wherein the user profile information includes demographic information associated with at least one user.

17. The method of claim 10, wherein the external information includes at least one of schedule information, calendar information and weather information.

18. The method of claim 10, further comprising:
defining, by the computing device, as a function of a first portion of the sensed information, a baseline representing a condition of a person who is not engaged in activity; and
wherein the detection of the user being engaged in an activity is based at least in part on a detection in a change from the baseline.

* * * * *